Sept. 16, 1958 J. M. BATCHELOR Plant Pat. 1,749
HOLLY PLANT
Filed Aug. 16, 1957
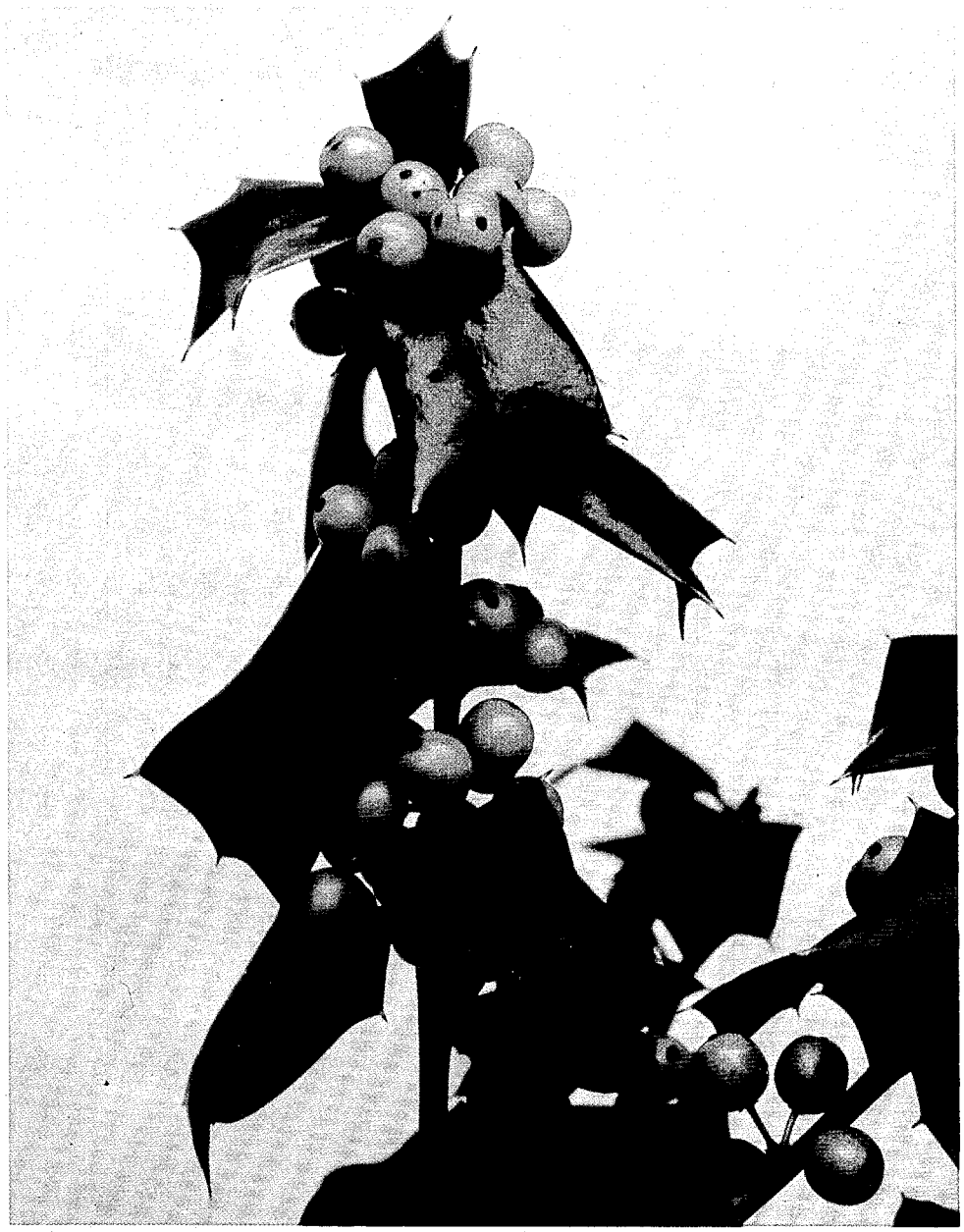
Inventor
Jackson M. Batchelor United States Patent Office Plant Pat. 1,749
Patented Sept. 16, 1958

1,749

HOLLY PLANT

Jackson Milton Batchelor, Pender County, N. C.

Application August 16, 1957, Serial No. 678,753

1 Claim. (Cl. 47—59)

My invention relates to a new and distinct variety of Chinese holly plant or *Ilex cornuta* which was produced by me as the result of a planned crossing of two unpatented parents of selection of *I. cornuta*. The male parent was a small-leaved selection and the female parent was a large-leaved selection having good fruit color, size and bearing qualities.

The primary objective of making the cross was to combine the characteristics of a small-leaved clone with that of an attractive, large-fruited and heavy-berried clone. Out of 110 seedlings resulting from this cross, one was selected which had the following qualities:

(1) Small and thick, dark green leaf characters.

(2) Production of large fruits which mature early in the summer.

(3) Fruits color in mid-October to early November so that a colorful berry crop is assured.

(4) Vigor of growth and dense, pyramidal upright habit.

(5) Insect and disease resistance to pests, common to the species, *I. cornuta*.

(6) The dark foliage color persists even with heavy production of fruit, which is not the case in the species.

This combination of characters definitely distinguishes my new variety from its parents as well as from all others of its class.

Asexual reproduction of my new variety by cuttings, as performed by me at Willard, North Carolina, shows that in over 4000 plants, so reproduced, the foregoing characteristics and distinctions come true to form and are established and transmitted through succeeding propagations.

The accompanying colored photograph shows the fruit and leaf qualities of a berried spray of my variety which distinguishes it from the species, *I. cornuta*, and the colors depicted are as nearly true as it is reasonably possible to reproduce today.

The following is a detailed description of my new variety, with color terminology in accordance with Ridgway's Color Standards and Nomenclature:

Type: Hardy, attractive, broad-leaf evergreen; for ornamental garden or commercial orchard planting.

Class: Hybrid *Ilex cornuta*.

Breeding: Seedling selection.

*Pollen Parent.*—Small-leaved *Ilex cornuta* selection.

*Seed Parent.*—Larger-leaved selection of the species having good color and size of fruit and bearing qualities.

Location where described specimens were grown: Willard, North Carolina.

Habit of Growth: Vigorous; dense; upright and pyramidal.

Foliage:

*Leaves.*—Glabrous, quadrangular-oblong with three strong spines of nearly equal size at the dilated apex and with one to two spines on each side of a truncate base; alternate; coriaceous, thick; dark and glossy green above; 1¾″ to 2¼″ long and ⅞″ to 1⅛″ wide; translucent leaf margin.

*Color.*—Mature: upper surface—Dark Dull Yellow Green, Plate XXXII, 31, *m*; under surface — Cress Green, Plate XXXI, 29, *k*. Young: upper surface—Cress Green, Plate XXXI, 29, *k*; under surface—Absinthe Green, Plate XXXI, 29—.

*Stem.*—New growth — Absinthe Green, Plate XXXI, 29—; old growth (one-year old)—Absinthe Green Plate XXXI, 29—; Three-year old—Buffy Brown, Plate XL, 17, *i*.

Flowers: Pistilate; calyx lobed; petals and ovaries 4; inconspicuous; usually borne in fascicles; white; late February to Early March; produced on previous season's growth.

Fruit: Spherical; ⅜″ to ⅝″ diameter; short clustered; Short pedicelled; profuse; Color—Spectrum Red, Plate I, *i*—.

Seed: Four; 3/16″ long; small; Color—Avellaneous, Plate XL, 17*b*.

Disease Resistance: Highly resistant to usual pests common to the species, e. g. scale, as determined by comparison with other *I. cornutas* and varieties of *I. opaca* and *I. aquifolium* grown under comparable cultural conditions at Willard, North Carolina.

Hardiness: Hardy without protection, particularly in Zones 28, 29, and 30 of the Climatic Provinces and Plant Growth Regions of the United States map published by the Soil Conservation Service, United States Department of Agriculture, Washington, D. C., in 1937. Subsequent zones of hardiness to be determined further in the future.

I claim:

A new and distinct variety of holly plant of the hybrid Cornuta class, substantially as herein shown and described, characterized particularly as to the small size of the thick dark-green leaves, the heavy production of large, attractive red fruits, the vigor and dense pyramidal habit and its inherent hardiness and resistance to disease pests.

References Cited in the file of this patent

UNITED STATES PATENTS

Pl. Pat. 1,322 Varden ---------- Nov. 16, 1954